(12) United States Patent
Hsieh et al.

(10) Patent No.: US 6,366,638 B1
(45) Date of Patent: Apr. 2, 2002

(54) METHODS AND APPARATUS FOR CT SCOUT IMAGE PROCESSING

(75) Inventors: Jiang Hsieh; Stanley H. Fox, both of Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/810,922

(22) Filed: Mar. 16, 2001

(51) Int. Cl.$^7$ ................................................ A61B 6/03
(52) U.S. Cl. ............................ 378/19; 378/4; 378/901; 382/132
(58) Field of Search ........................... 378/4, 19, 15, 378/901; 382/131, 132

(56) References Cited

U.S. PATENT DOCUMENTS

| | | |
|---|---|---|
| 5,265,013 A | * 11/1993 | King et al. ................... 378/4 |
| 5,491,735 A | 2/1996 | Hsieh |
| 5,515,409 A | 5/1996 | Hsieh |
| 5,757,951 A | * 5/1998 | Tuy ............................ 382/131 |
| 6,023,494 A | 2/2000 | Senzig et al. |
| 6,038,278 A | 3/2000 | Hsieh et al. |
| 6,061,419 A | 5/2000 | Hsieh et al. |
| 6,108,575 A | 8/2000 | Besson |
| 6,295,331 B1 | * 9/2001 | Hsieh .......................... 378/19 |

* cited by examiner

Primary Examiner—Drew Dunn
(74) Attorney, Agent, or Firm—Carl B. Horton, Esq.; Armstrong Teasdale LLP

(57) ABSTRACT

Methods and Apparatus for reducing image artifacts when reconstructing an image with a multislice computed tomographic (CT) imaging scanner are provided. Scout images are generated by obtaining a plurality of projection views of an object, modifying the projection data utilizing a deconvolution kernel, generating a horizontal gradient and a vertical gradient based on the modified projection data, applying helical weights to the horizontal gradient and vertical gradient, and applying a desired level of enhancement to the weighted horizontal and vertical gradients.

42 Claims, 2 Drawing Sheets

METHODS AND APPARATUS FOR CT SCOUT IMAGE PROCESSING

BACKGROUND OF THE INVENTION

This invention relates generally to methods and apparatus for CT imaging and other radiation imaging systems and, more particularly, to utilizing a generalized helical interpolation algorithm.

In at least some "computed tomography" (CT) imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed.

In at least one known imaging system, a single scout image is generated by fixing the position of the x-ray source and translating the object in a z-axis direction. A resulting scout image, often called a scanogram, is similar to a plain radiography image. Using the scout image, an operator may identify anatomical landmarks. However, the scout image generated from a single projection angle does not provide depth information regarding the object anatomy.

A plurality of scout scans are performed to generate depth information scout images of an object. Specifically, in order to generate at least one depth information scout image, the imaging system performs each scout scan at a different projection angle, or scout angle, with respect to the scanned object, e.g., patient. For example, as the patient is translated along a z-axis at a constant speed, a plurality of scout, or projection, data is collected as the position of a gantry is adjusted along a plurality of projection angles, or scout angles.

Typically an urology x-ray examination can take up to five hours to complete. A series of x-ray films need to be taken prior to injecting contrast media into a patient and following uptake of the contrast media. The x-ray procedure is lengthy and tedious because it takes several hours for the contrast media to be eliminated from the patient's system. In another known application, a CT scanner and an x-ray are is used to improve diagnostic accuracy and improve the examination time. The protocol requires a combined set of planar x-ray films and CT scans. A special tabletop is placed on top of the existing CT table so that a film cassette can be placed underneath, and an x-ray tube is suspended on a ceiling above a patient table. A first set of x-ray film and CT helical scans are taken, prior to the administration of contrast media or as the contrast media is injected into the patient's abdominal area but before the contrast media is sufficiently absorbed by the patient to impact collected data. The abdominal area is compressed by an inflated balloon to keep the contrast media within the kidneys and the upper urinary tracks. After the contrast media is absorbed by the patient, i.e., uptake of contrast media, a second set of x-ray film and CT scans is taken. The compression apparatus is then removed allowing the contrast media to leave the kidneys and upper urinary tracks, and the x-ray film and CT scans are repeated approximately thirty to forty minutes after the injection of the contrast medium.

Known CT scout images, however, include dark bands near high-density structures, e.g., bones. These dark bands, or artifacts, prevent accurate assessment of the patient's pathology when the artifacts are near contrast filled vessels. The artifacts are caused by the known enhancement algorithm utilized in typical scout processing. This known algorithm sums multiple samples along the table travel direction for noise suppression. As a result, the spatial resolution in the z-direction, e.g., the direction of table travel, is compromised. Further, a significant mismatch between an x-resolution and z-resolution results when the minimum slice thickness, e.g., size of each sample in the z-direction, is 1.25 mm. The x-ray device can be eliminated and the CT scanner can be solely utilized to generate CT scout images.

BRIEF SUMMARY OF THE INVENTION

Methods and Apparatus for reducing image artifacts when reconstructing an image with a multislice computed tomographic (CT) imaging scanner are provided. In an exemplary embodiment of the method, scout images are generated by obtaining a plurality of projection views of an object, modifying the projection data utilizing a deconvolution kernel, generating a horizontal gradient and a vertical gradient based on the modified projection data, applying weights to the horizontal gradient and vertical gradient, and applying a desired level of enhancement to the weighted horizontal and vertical gradients. The above described method generates enhanced scout images without requiring modifying the CT scanner.

In one aspect, an imaging system comprises a computer, a gantry having a detector array, an x-ray source for radiating an x-ray beam toward the detector array, and the imaging system acquires a plurality of projection views of the same projection angle of the object. The imaging system modifies the projection data utilizing a deconvolution kernel, generates a horizontal gradient and a vertical gradient based on the modified projection data, applies weights to the horizontal gradient and vertical gradient. and applies a desired level of enhancement to the weighted horizontal and vertical gradients to generate a scout image.

In another aspect, a processor in the imaging system is programmed to acquire projection data for a plurality of projection views of the object. The processor modifies the projection data utilizing a deconvolution kernel, generates a horizontal gradient and a vertical gradient based on the modified projection data, applies weights to the horizontal gradient and vertical gradient, and applies a desired level of enhancement to the weighted horizontal and vertical gradients to generate scout images.

In yet another aspect, a computer-readable medium in the imaging system is provided which comprises records of projection data for a plurality of projection views that are used to reconstruct a plurality of records of scout images. To generate the plurality of records of scout images the records of projection data are modified utilizing a deconvolution kernel, records of horizontal and vertical gradients are generated based on the records of modified projection data, a plurality of rules apply relative weights to the records of horizontal and vertical gradients, and a plurality of rules apply a desired level of enhancement to the records of weighted horizontal and vertical gradients.

DETAILED DESCRIPTION OF THE INVENTION

Figure 1:
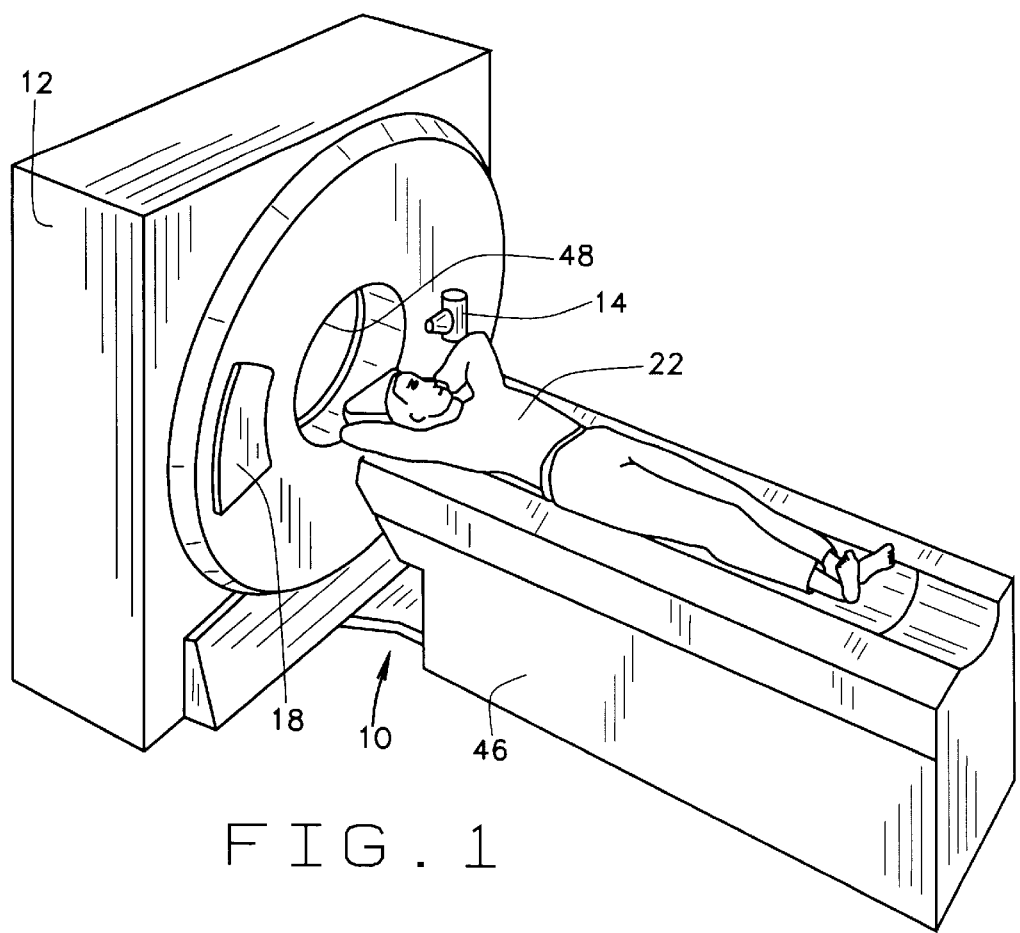
FIG. 1 is a pictorial view of a CT imaging system.
Figure 2:
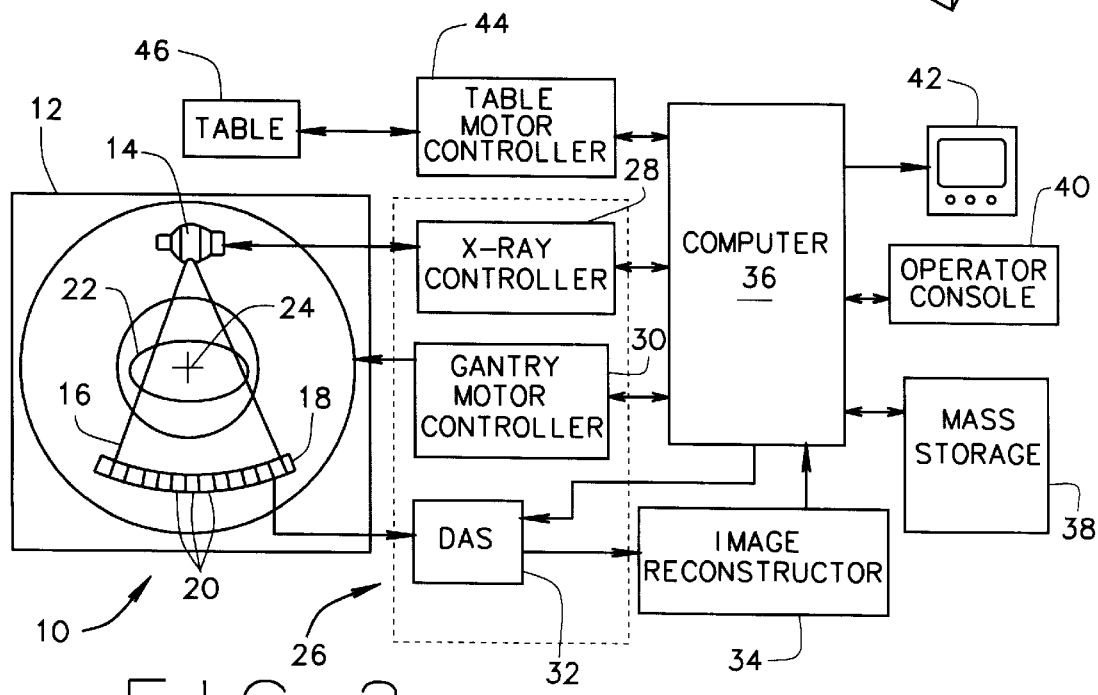
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
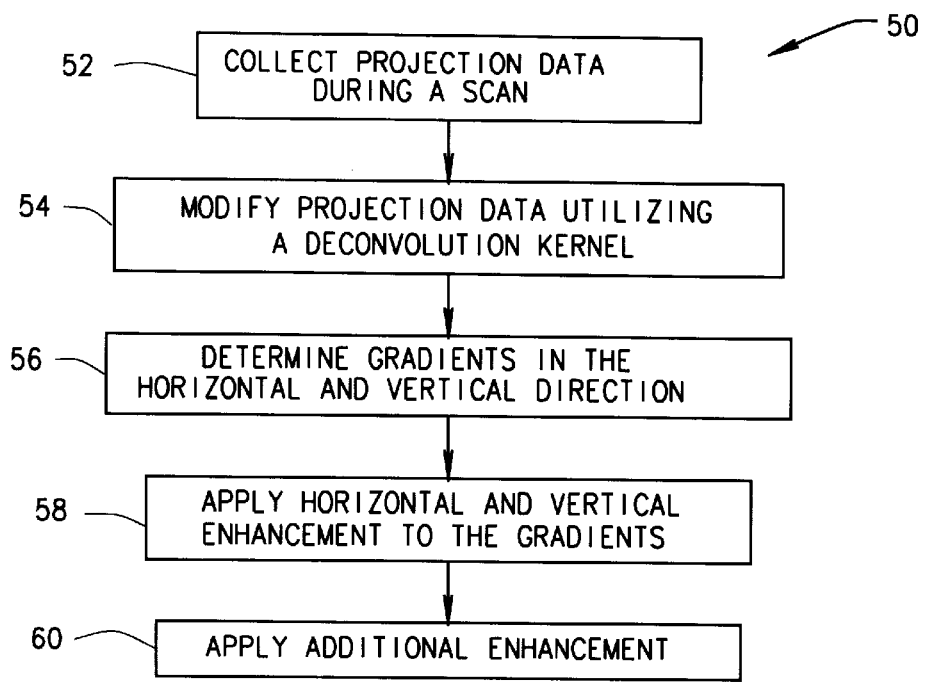
FIG. 3 is a flow chart illustrating the steps executed by the CT system for Scout image processing.

FIG. 3 is a flow chart 50 illustrating the steps to improve spatial resolution during scout image processing. The method illustrated in FIG. 3 can be practiced by DAS 32 (shown in FIG. 2), image reconstructor 34 (shown in FIG. 2), or computer 36 (shown in FIG. 2). Generally, a processor in at least one of DAS 32, reconstructor 34, and computer 36 is programmed to execute the process steps described below. Of course, the method is not limited to practice in CT system 10 and can be utilized in connection with many other types and variations of imaging systems.

Referring specifically to FIG. 3, a set of raw scan data is acquired 52 during a scan, and the raw data is pre-processed to produce a projection. The data is resolved 54 in the z-direction to approximately the same resolution as the horizontal direction to be equivalent in resolution to a planar image. Then, a horizontal gradient and a vertical gradient are determined 56 by determining a variation between samples in the horizontal and vertical direction. Weights are calculated based on the horizontal and vertical variance. Different weights are then applied to the horizontal and vertical gradients and a desired amount of enhancement is applied 58 to the weighted gradients. Then, additional enhancement is applied 60.

During scout scanning, gantry 12 is not rotated but remains stationary while table 46 moves through gantry opening 48. Referring specifically to FIG. 3, projection data is acquired 52 for a view from a particular gantry angle relative to patient 22 as patient table 46 travels at 50 mm/s in the z-axis direction while DAS 32 samples at 500 Hz. In one embodiment, approximately twelve projection views are collected per detector cell thickness. Then, six adjacent views are summed to obtain an inter-pixel distance that is approximately equal to a sampling distance in an x-direction, e.g., horizontal direction. The distance between adjacent samples near the iso-center is approximately 0.58 mm because of the magnification of the fan beam sampling geometry. The simple summation process will degrade the z-axis resolution, e.g., vertical resolution, which is already significantly worse than the x-axis direction resolution, e.g., horizontal resolution, without the summation.

To improve spatial resolution, a deconvolution process is utilized. A modified sample, p'(i,j), is obtained by convolving an original sample, p(i,j), with a deconvolution kernel, θ(j), to reduce an effective thickness below a detector aperture size of 1.25 mm according to the relationship:

$$p'(i,j) = p(i,j) \otimes \theta(i,j), \quad (1)$$

where i represents the index in the channel direction, and j represents the index in the view direction. p'(i,j) represents the projection reading of channel i and view j, after proper calibration: e.g., offset correction, air calibration, reference normalization, minus logarithm, and beam hardening. The modified sample, p'(i, j), ignores the multi-slice nature of sampling because the samples acquired by different detector rows are combined into a single set of samples after a proper sampling delay. For example, in an exemplary embodiment, a sample is collected every 0.1 mm. For a detector aperture of 1.25 mm, samples from a neighboring row can be integrated into the current row sampling by a delay or advance of 12.5 samples. In one embodiment, the samples from the neighboring row are averaged with the current row using simple interpolation. In another embodiment, the samples are treated as additional samples that straddle the previous samples, which effectively doubles the sampling rate.

Many techniques can be utilized to derive the deconvolution kernel, $\theta(j)$. For example, in one embodiment, a "singular value decomposition" (SVD) technique is utilized to derive the kernel based on a system point spread function. In an alternative embodiment, the first n views, e.g., n<6, is summed from a set of intermediate samples to reduce image noise. These intermediate samples are then processed with a deconvolution kernel to generate a set of samples with improved spatial resolution. For example, in one of the preferred embodiments, three views are summed. Within the three views, the maximum deviation from the center sample is only 0.1 mm; therefore, the impact on spatial resolution is kept to a minimum. A five-point deconvolution kernel is then applied to these samples to arrive at the enhanced samples. In an alternative embodiment, the deconvolution processing can be carried out in frequency space. A Fourier transform of an original scout is obtained multiplied by a deconvolution filter. The result is then processed though an inverse Fourier transform to produce an enhanced scout.

To enhance a small structure present in the scanned object. To avoid ringing artifacts, the direction along which the enhancement takes place needs to be determined. The variation in both an x-axis direction, e.g., channel direction, and an z-axis direction, e.g., view direction, are measured. For example, in one embodiment, a standard deviation is used as a measure of variation. In an exemplary embodiment, the difference between the averaged sample set and the sample itself is selected to be used as an indication of signal variation. Mathematically, the variation in a horizontal and vertical directions, $\xi_x(i,j)$ and $\xi_z(i,j)$, is expressed by the following gradient equations:

$$\xi_x(i, j) = |p'(i, j) - \psi_i(i, j)| = \left| p'(i, j) - \frac{1}{2N+1} \sum_{k=i-N}^{i+N} p'(k, j) \right|, \quad (2)$$

$$\xi_z(i, j) = |p'(i, j) - \psi_j(i, j)| = \left| p'(i, j) - \frac{1}{2M+1} \sum_{k=j-M}^{j+M} p'(i, k) \right|, \quad (3)$$

where p'(i,j) represents a projection reading sample of channel i and view j, $\psi_i(i,j)$ is an average of a sample in two different directions j, $\psi_j(i,j)$ N and M are the number of points over which the sample is averaged, and k is a variable used to index samples.

In one embodiment, the gradients are enhanced in both the horizontal and vertical directions to ensure the enhancement process does not lead to overshoot and undershoot. A directional "un-sharp masking" process is utilized. An enhanced scout, $\epsilon(i,j)$, is determined by the following relationship:

$$\varepsilon(i, j) = p'(i, j) - \frac{\alpha \psi_i(i, j)\xi_z(i, j)}{\xi_x(i, j) + \xi_z(i, j)} - \frac{\alpha \psi_j(i, j)\xi_x(i, j)}{\xi_x(i, j) + \xi_z(i, j)}, \quad (4)$$

where $\alpha$ is a parameter that adjusts the amount of enhancement, $\psi_i(i,j)$ is an average sample in the horizontal direction, $\psi_j(i,j)$ is an average sample in the vertical direction, where $$\frac{\xi_x(i, j)}{\xi_x(i, j) + \xi_z(i, j)} \text{ and } \frac{\xi_z(i, j)}{\xi_x(i, j) + \xi_z(i, j)}$$

are a relative weights, wherein $\xi_x(i,j)$ is the gradient variation in the horizontal direction, $\xi_z(i,j)$ is the gradient variation in the vertical direction. In an exemplary embodiment, suitable images are achieved when $\alpha=0.3$, and the parameters N and M are selected such that N=M=9. In one embodiment, a range of values for $\alpha$ is from zero to one, and a desirable working range is $0.2<\alpha<0.4$.

In an alternative embodiment, additional enhancement can be applied in either the horizontal direction or both the horizontal and vertical direction of the scout image. Further enhancement can be achieved by selecting different kernel sizes. For example, in one embodiment, the scout image is further enhanced in a horizontal direction, e.g., in the x-direction, according to:

$$\eta(i,j)=c[\epsilon(i,j)\otimes \zeta(i)]+(1-c)\epsilon(i,j), \quad (5)$$

where $\epsilon(i,j)$ is the enhanced scout, $\eta(i,j)$ is a further enhanced scout in the horizontal direction, $\zeta(i)$ is a five-point deconvolution kernel, and c is a parameter used to control the amount of enhancement. In an exemplary embodiment, c is selected such that c=0.15.

In another embodiment, additional enhancement can be applied to the scout image in the vertical direction. After the scout image has been enhanced in the horizontal direction, e.g., $\eta(i,j)$ has been generated. $\eta(i,j)$ is utilized to further enhance the scout image in the vertical direction according to:

$$\mu(i,j)=d[\eta(i,j)\otimes \zeta(i)]+(1-d)\eta(i,j), \quad (6)$$

where $\mu(i,j)$ is the scout image further enhanced in both the horizontal and vertical direction, $\eta(i,j)$ is the enhanced scout in the horizontal direction, $\zeta(i)$ is a five-point deconvolution kernel, and d is a parameters used to control the amount of enhancement. In an exemplary embodiment, d is selected such that d=0.15. In one embodiment, increased enhancement is utilized to increase image resolution of small pathologies, such as kidney stones having low density. By utilizing enhanced scout images overshoot and undershoot are essentially eliminated, and the image does not appear to be artificial; but has a "look" of a typical x-ray film.

Figure 4:
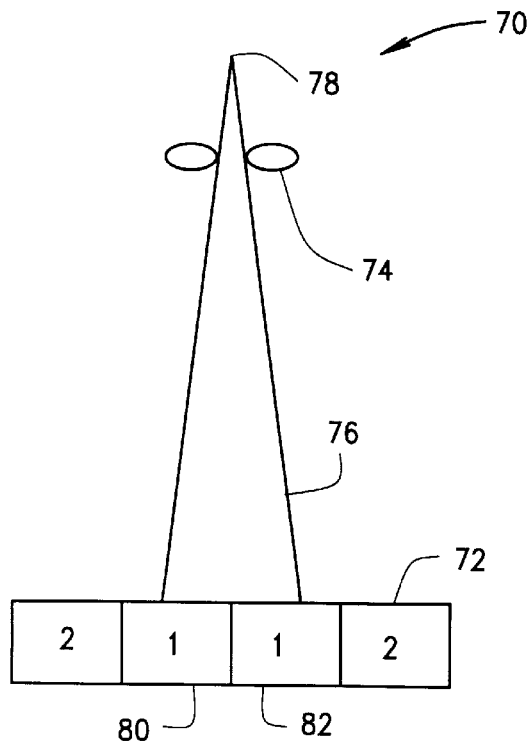
FIG. 4 is a drawing showing a pre-patient collimator being utilized to collimate an x-ray beam to minimize slice thickness.

In another embodiment, a two dimensional kernel can be utilized to increase the speed of processing the enhanced scout image. To further improve the spatial resolution of the scout image, a thin-twin configuration, e.g., a CT system utilizing collimators having at least one 1 mm aperture, could be utilized during generation of scout images. For a multi-slice CT scanner, the smallest slice thickness is determined mainly by the detector cell aperture. Specifically referring to FIG. 4, in one embodiment, a minimum slice thickness of 1.25 mm is utilized during scout data acquisition utilizing a quad-detector 72. To significantly improve the spatial resolution in the z-direction, a pre-patient collimator 74 is utilized, in one embodiment, to collimate an x-ray beam 76, generated from an x-ray source 78, directed to a fraction of the center two detector-rows 80 and 82. In this manner, the slice thickness is no longer determined by the detector cell aperture. Then the enhancement process is performed as described above.

In yet another embodiment, a CT system 10 includes a computer program residing on a computer-readable medium within mass storage 38 for reconstructing the image. A plurality of records of projection data for a plurality of projection views are used to reconstruct a plurality of records of scout images. To generate the plurality of records of scout images the records of projection data are modified utilizing a deconvolution kernel. In one embodiment a five-point deconvolution kernel is utilized. Of course, other sizes of kernels can be used. Records of horizontal and vertical gradients are generated based on the records of modified projection data. A plurality of rules apply relative weights to the records of horizontal and vertical gradients, and a plurality of rules apply a desired level of enhancement to the records of weighted horizontal and vertical gradients.

While the invention has been described in terms of various specific embodiments, those skilled in the art will recognize that the invention can be practiced with modification within the spirit and scope of the claims.

What is claimed is:

1. A method for reconstructing scout images using a computed tomography imaging system, said method comprising the steps of:

scanning an object to obtain projection data for at least one scout scan;

modifying projection data utilizing a deconvolution kernel;

determining a horizontal gradient and a vertical gradient using the modified projection data;

applying desired levels of enhancement based on the horizontal and vertical gradients; and generating a plurality of scout images based on the modified projection data and horizontal and vertical gradients.

2. A method in accordance with claim 1 wherein said step of modifying projection data comprises the step of modifying projection data according to the relationship:

$$p'(i,j) = p(i,j) \otimes \theta(j),$$

where $p(i,j)$ is a sample of projection data with i representing an index in the channel direction and j representing an index in a view direction and $\theta(j)$ is a deconvolution kernel.

3. A method in accordance with claim 2 wherein the deconvolution kernel comprises a five-point deconvolution kernel.

4. A method in accordance with claim 2 wherein the horizontal gradient comprises the relationship:

$$\xi_x(i,j) = |p'(i,j) - \psi_i(i,j)|,$$

where $p'(i,j)$ is projection data of a channel i and a view j, $\psi_i(i,j)$ is an average of a sample in a horizontal direction.

5. A method in accordance with claim 4 wherein the average of a sample in a horizontal direction, $\psi_i(i,j)$, comprises the relationship:

$$\psi_i(i,j) = \frac{1}{2N+1} \sum_{k=i-N}^{i+N} p'(k,j),$$

where $p'(j,k)$ is a sample of projection data of a view j and a channel k, and N is the number of points over which the sample is averaged in the horizontal direction.

6. A method in accordance with claim 2 wherein the vertical gradient comprises the relationship:

$$\xi_z(i,j) = |p'(i,j) - \psi_j(i,j)|,$$

where $p'(i,j)$ is a sample of projection data of a channel i and a view j, and $\psi_j(i,j)$ is an average of a sample in a vertical direction.

7. A method in accordance with claim 6 wherein the average of a sample in a vertical direction, $\psi_j(i,j)$, comprises the relationship:

$$\psi_j(i,j) = \frac{1}{2M+1} \sum_{k=j-M}^{j+M} p'(i,k),$$

where $p'(i,k)$ is a sample of projection data of a channel i and a view k, and M is the number of points over which the sample is averaged in the vertical direction.

8. A method in accordance with claim 1 wherein said step of applying a relative weight comprises the step of determining a relative weight in the horizontal direction according to the relationship:

$$\frac{\xi_z(i,j)}{\xi_x(i,j) + \xi_z(i,j)},$$

where $\xi_z(i,j)$ is the vertical gradient and $\epsilon_x(i,j)$ is the horizontal gradient.

9. A method in accordance with claim 1 wherein said step of applying a relative weight comprises the step of determining a relative weight in the vertical direction according to the relationship:

$$\frac{\xi_x(i,j)}{\xi_x(i,j) + \xi_z(i,j)},$$

where $\xi_z(i,j)$ is a vertical gradient and $\xi_x(i,j)$ is a horizontal gradient.

10. A method in accordance with claim 5 wherein said step of applying relative weights comprises the step of applying relative weights in the horizontal direction to the average sample $\psi_i(i,j)$, according to the relationship:

$$\frac{\alpha \psi_i(i,j) \xi_z(i,j)}{\xi_x(i,j) + \xi_z(i,j)},$$

where $\psi_i(i,j)$ is the average of a sample in the horizontal direction, $\xi_z(i,j)$ is the vertical gradient, $\xi_x(i,j)$ is the horizontal gradient, and $\alpha$ is a parameter that adjusts the amount of enhancement.

11. A method in accordance with claim 7 wherein said step of applying relative weights comprises the step of applying relative weights in the vertical direction to the average sample, $\psi_j(i,j)$, according to the relationship:

$$\frac{\alpha \psi_j(i,j)\xi_x(i,j)}{\xi_x(i,j)+\xi_z(i,j)},$$

where $\psi_j(i,j)$ is an average of a sample in the vertical direction, $\xi_z(i,j)$ is the vertical gradient, $\xi_x(i,j)$ is the horizontal gradient, and $\alpha$ is a parameter that adjusts the amount of enhancement.

12. A method according to claim 2 wherein the scout image comprises the relationship:

$$\varepsilon(i,j) = p'(i,j) - \frac{\alpha \psi_i(i,j)\xi_z(i,j)}{\xi_x(i,j)+\xi_z(i,j)} - \frac{\alpha \psi_j(i,j)\xi_x(i,j)}{\xi_x(i,j)+\xi_z(i,j)},$$

where $\alpha$ is a parameter that adjusts the amount of enhancement, $\psi_i(i,j)$ is an average sample in the horizontal direction, $\psi_j(i,j)$ is an average sample in the vertical direction, where $$\frac{\xi_x(i,j)}{\xi_x(i,j)+\xi_z(i,j)} \text{ and } \frac{\xi_z(i,j)}{\xi_x(i,j)+\xi_z(i,j)}$$

and are a relative weights,
wherein $\xi_x(i,j)$ is the horizontal gradient, and $\xi_z(i,j)$ is the vertical gradient.

13. A method according to claim 12 wherein said step of applying a desired level of enhancement comprises the step of enhancing the scout image in a horizontal direction according to the relationship:

$$\eta(i,j)=c[\varepsilon(i,j)\otimes \zeta(i)]+(1-c)\varepsilon(i,j),$$

where $\varepsilon(i,j)$ is the scout image, $\zeta(i)$ is a five-point deconvolution kernel, and c is a parameter used to control the amount of enhancement.

14. A method according to claim 13 wherein said step of applying a desired level of enhancement comprises the step of enhancing the scout image in a vertical direction according to the relationship:

$$\mu(i,j)=d[\eta(i,j)\otimes \zeta(i)]+(1-d)\eta(i,j),$$

where $\eta(i,j)$ is the scout image enhanced in the horizontal direction, $\zeta(i)$ is a five-point deconvolution kernel, and d is a parameter used to control the amount of enhancement.

15. An imaging system for generating scout images of an object, said computed tomography system comprising a computer, a gantry having a detector array, an x-ray source for radiating an x-ray beam along an imaging plane toward a detector array including a plurality of detector cells, the computer coupled to the x-ray source and the gantry, said system configured to:
- scan an object to obtain projection data for at least one scout scan;
- modify said projection data utilizing a deconvolution kernel;
- determine a horizontal gradient and a vertical gradient using said modified projection data;
- apply desired levels of enhancement to said horizontal and vertical gradients; and
- generate a plurality of scout images based on said modified projection data and horizontal and vertical gradients.

16. An imaging system in accordance with claim 15 wherein projection data is modified according to the relationship:

$$p'(i,j)=p(i,j)\otimes \theta(j),$$

where $p(i,j)$ is a sample of projection data with i representing an index in a channel direction and j representing an index in a view direction and $\theta(j)$ is a deconvolution kernel.

17. An imaging system in accordance with claim 16 wherein said deconvolution kernel comprises a five-point deconvolution kernel.

18. An imaging system in accordance with claim 16 wherein said horizontal gradient comprises the relationship:

$$\xi_x(i,j)=|p'(i,j)-\psi_i(i,j)|,$$

where $p'(i,j)$ is said sample of projection data of a channel i and a view j, $\psi_i(i,j)$ is an average of a sample in the horizontal direction.

19. An imaging system in accordance with claim 18 wherein said average of the sample in a horizontal direction, $\psi_i(i,j)$, comprises the relationship:

$$\psi_i(i,j) = \frac{1}{2N+1}\sum_{k=i-N}^{i+N} p'(k,j),$$

where $p'(j,k)$ is said sample of projection data of a view j and a channel k, and N is the number of points over which the sample is averaged in the horizontal direction.

20. An imaging system in accordance with claim 16 wherein said vertical gradient comprises the relationship:

$$\xi_z(i,j)=|p'(i,j)-\psi_j(i,j)|,$$

where $p'(i,j)$ is said sample of projection data of a channel i and a view j, and $\psi_j(i,j)$ is an average of a sample in the vertical direction.

21. An imaging system in accordance with claim 16 wherein said average of the sample in a vertical direction, $\psi_j(i,j)$, comprises the relationship:

$$\psi_j(i,j) = \frac{1}{2M+1}\sum_{k=j-M}^{j+M} p'(i,k),$$

where $p'(i,k)$ is a sample of projection data of a channel i and a view k, and M is the number of points over which the sample is averaged in the vertical direction.

22. An imaging system in accordance with claim 15 wherein said relatives weights in a horizontal direction comprises the relationship:

$$\frac{\xi_z(i,j)}{\xi_x(i,j)+\xi_z(i,j)},$$

where $\xi_z(i,j)$ is said vertical gradient and $\xi_x(i,j)$ is said horizontal gradient.

23. An imaging system in accordance with claim 15 wherein said relative weights in the vertical direction comprises the relationship:

$$\frac{\xi_x(i,j)}{\xi_x(i,j)+\xi_z(i,j)},$$

where $\xi_z(i,j)$ is said vertical gradient and $\xi_x(i,j)$ is said horizontal gradient.

24. An imaging system in accordance with claim 19 wherein said average sample weighted in the horizontal direction comprises the relationship:

$$\frac{\alpha \psi_i(i,j)\xi_z(i,j)}{\xi_x(i,j)+\xi_z(i,j)},$$

where $\psi_i(i,j)$ is an average of a sample in the horizontal direction, $\xi_z(i,j)$ represents the vertical gradient, $\xi_x(i,j)$ is represents the horizontal gradient, and $\alpha$ is a parameter that adjusts the amount of enhancement.

25. An imaging system in accordance with claim 21 wherein said average sample weighted in the vertical direction comprises the relationship:

$$\frac{\alpha \psi_j(i,j)\xi_x(i,j)}{\xi_x(i,j)+\xi_z(i,j)},$$

where $\psi_j(i,j)$ is an average of a sample in the vertical direction, $\xi_z(i,j)$ represents the vertical gradient, $\xi_x(i,j)$ is represents the horizontal gradient, and $\alpha$ is a parameter that adjusts the amount of enhancement.

26. An imaging system in accordance with claim 16 wherein said scout image comprises the relationship:

$$\varepsilon(i,j) = p'(i,j) - \frac{\alpha \psi_i(i,j)\xi_z(i,j)}{\xi_x(i,j)+\xi_z(i,j)} - \frac{\alpha \psi_j(i,j)\xi_x(i,j)}{\xi_x(i,j)+\xi_z(i,j)},$$

where $\alpha$ is a parameter that adjusts the amount of enhancement, $\psi_i(i,j)$ is said average sample in the horizontal direction, $\psi_j(i,j)$ is said average sample in the vertical direction, where $$\frac{\xi_x(i,j)}{\xi_x(i,j)+\xi_z(i,j)} \text{ and } \frac{\xi_z(i,j)}{\xi_x(i,j)+\xi_z(i,j)}$$

are said relative weights, wherein $\xi_x(i,j)$ is said horizontal gradient and $\xi_z(i,j)$ is said vertical gradient.

27. An imaging system in accordance with claim 26 wherein said scout image enhanced in the horizontal direction comprises the relationship:

$$\eta(i,j)=c[\varepsilon(i,j)\otimes \zeta(i)]+(1-c)\varepsilon(i,j),$$

where $\varepsilon(i,j)$ is said scout image, $\zeta(i)$ is a five-point deconvolution kernel, and c is a parameter used to control the amount of enhancement.

28. An imaging system in accordance with claim 27 wherein said scout image enhanced in the horizontal and vertical directions comprises the relationship:

$$\eta(i,j)=d[\eta(i,j)\otimes \zeta(i)]+(1-d)\eta(i,j),$$

where $\eta(i,j)$ is said scout image enhanced in the horizontal direction, $\zeta(i)$ is a five-point deconvolution kernel, and d is a parameter used to control the amount of enhancement.

29. A processor programmed to reconstruct scout images in a computed tomography system, said processor configured to:

modify projection data utilizing a five-point deconvolution kernel;

determine a horizontal gradient and a vertical gradient using said modified projection data;

apply desired levels of enhancement to said horizontal and vertical gradients; and generate a plurality of scout images based on said modified projection data and horizontal and vertical gradients.

30. A processor programmed according to claim 29 wherein said projection data is modified according to the relationship:

$$p'(i,j)=p(i,j)\otimes \theta(j),$$

where $p(i,j)$ is a sample of projection data with i representing an index in a channel direction and j representing an index in a view direction and $\theta(j)$ is a deconvolution kernel.

31. A processor programmed according to claim 30 wherein said horizontal gradient comprises the relationship:

$$\xi_x(i,j) = \left| p'(i,j) - \frac{1}{2N+1}\sum_{k=i-N}^{i+N} p'(k,j) \right|,$$

where $p'(i,j)$ is a sample of projection data of a channel i and a view j, $p'(j,k)$ is a sample of projection data of a view j and a channel k, and N is the number of points over which the sample is averaged in the horizontal direction.

32. A processor programmed according to claim 30 wherein said vertical gradient comprises the relationship:

$$\xi_z(i,j) = \left| p'(i,j) - \frac{1}{2M+1}\sum_{k=j-M}^{j+M} p'(i,k) \right|,$$

where $p'(i,j)$ is a sample of projection data of channel i and view j, $p'(i,k)$ is a sample of projection data of a channel i and a view k, and M is the number of points over which the sample is averaged in the vertical direction.

33. A processor programmed according to claim 30 wherein said scout image comprises the relationship:

$$\varepsilon(i,j) = p'(i,j) - \frac{\alpha \psi_i(i,j)\xi_z(i,j)}{\xi_x(i,j)+\xi_z(i,j)} - \frac{\alpha \psi_j(i,j)\xi_x(i,j)}{\xi_x(i,j)+\xi_z(i,j)},$$

where $\alpha$ is a parameter that adjusts the amount of enhancement, $\psi_i(i,j)$ is an average sample in the horizontal direction, $\psi_j(i,j)$ is an average sample in the vertical direction, where $$\frac{\xi_x(i,j)}{\xi_x(i,j)+\xi_z(i,j)} \text{ and } \frac{\xi_z(i,j)}{\xi_x(i,j)+\xi_z(i,j)}$$

are said relative weights, wherein $\xi_x(i,j)$ is horizontal gradient, and $\xi_z(i,j)$ is said vertical gradient.

34. A processor programmed according to claim 33 wherein said scout image enhanced in the horizontal direction comprises the relationship:

$$\eta(i,j)=c[\varepsilon(i,j)\otimes \zeta(i)]+(1-c)\varepsilon(i,j),$$

where $\varepsilon(i,j)$ is said enhanced scout, $\zeta(i)$ is a five-point deconvolution kernel, and c is a parameter used to control the amount of enhancement.

35. A processor programmed according to claim 34 wherein said scout image enhanced in the horizontal and vertical direction comprises the relationship:

$$\mu(i,j)=d[\eta(i,j)\otimes \zeta(i)]+(1-d)\eta(i,j),$$

where $\eta(i,j)$ is said scout image enhanced in the horizontal direction, $\zeta(i)$ is a five-point deconvolution kernel, and d is a parameter used to control the amount of enhancement.

36. A computer-readable medium in an imaging system, said computer-readable medium comprising:

records of projection data for a plurality of projection views;

records of modified projection data based on said records of projection data modified by a five-point deconvolution kernel;

records of horizontal and vertical gradients based on records of modified projection data;

a plurality of rules to apply desired levels of enhancement to said records of horizontal and vertical gradients; and a plurality of rules to reconstruct records of scout images based on said modified projection data and horizontal and vertical gradients.

37. A computer-readable medium according to claim 36 wherein said projection data is modified according to the relationship:

$$p'(i,j) = p(i,j) \otimes \theta(j),$$

where $p(i,j)$ is a sample of projection data with i representing an index in a channel direction and j representing an index in a view direction and $\theta(j)$ is a deconvolution kernel.

38. A computer-readable medium according to claim 37 wherein said horizontal gradient comprises the relationship:

$$\xi_x(i, j) = \left| p'(i, j) - \frac{1}{2N+1} \sum_{k=i-N}^{i+N} p'(k, j) \right|,$$

where $p'(i,j)$ is a sample of projection data of a channel i and a view j, $p'(j,k)$ is a sample of projection data of a view j and a channel k, and N is the number of points over which the sample is averaged in the horizontal direction.

39. A computer-readable medium according to claim 37 wherein said vertical gradient comprises the relationship:

$$\xi_z(i, j) = \left| p'(i, j) - \frac{1}{2M+1} \sum_{k=j-M}^{j+M} p'(i, k) \right|,$$

where $p'(i,j)$ is a sample of projection data of channel i and view j, $p'(i,k)$ is a sample of projection data of a channel i and a view k, and M is the number of points over which the sample is averaged in the vertical direction.

40. A computer-readable medium according to claim 37 wherein said scout image comprises the relationship:

$$\varepsilon(i, j) = p'(i, j) - \frac{\alpha \psi_i(i, j)\xi_z(i, j)}{\xi_x(i, j) + \xi_z(i, j)} - \frac{\alpha \psi_j(i, j)\xi_x(i, j)}{\xi_x(i, j) + \xi_z(i, j)},$$

where $\alpha$ is a parameter that adjusts the amount of enhancement, $\psi_i(i,j)$ is an average sample in the horizontal direction, $\psi_j(i,j)$ is an average sample in the vertical direction, where $$\frac{\xi_x(i, j)}{\xi_x(i, j) + \xi_z(i, j)} \text{ and } \frac{\xi_z(i, j)}{\xi_x(i, j) + \xi_z(i, j)}$$

are said relative weights, wherein $\xi_x(i,j)$ is horizontal gradient, and $\xi_z(i,j)$ is said vertical gradient.

41. A computer-readable medium according to claim 40 wherein said scout image enhanced in the horizontal direction comprises the relationship:

$$\eta(i,j) = c[\epsilon(i,j) \otimes \zeta(i)] + (1-c)\epsilon(i,j),$$

where $\epsilon(i,j)$ is said enhanced scout, $\zeta(i)$ is a five-point deconvolution kernel, and c is a parameter used to control the amount of enhancement.

42. A computer-readable medium according to claim 41 wherein said scout image enhanced in the horizontal and vertical direction comprises the relationship:

$$\mu(i,j) = d[\eta(i,j) \otimes \zeta(i)] + (1-d)\eta(i,j),$$

where $\eta(i,j)$ is said scout image enhanced in the horizontal direction, $\zeta(i)$ is a five-point deconvolution kernel, and d is a parameter used to control the amount of enhancement.

* * * * *

UNITED STATES PATENT AND TRADEMARK OFFICE
CERTIFICATE OF CORRECTION

PATENT NO.    : 6,366,638 B1
DATED         : April 2, 2002
INVENTOR(S)   : Hsieh et al.

It is certified that error appears in the above-identified patent and that said Letters Patent is hereby corrected as shown below:

Column 8,
Line 15, delete "$\Psi_i(i,j)$" and insert therefor -- $\Psi_j(i,j)$ --.
Line 38, delete "$\varepsilon_x(i,j)$" and insert therefor -- $\xi_x(i,j)$ --.

Column 9,
Line 25, delete "and are a relative weights," and insert therefor -- are relative weights, --.

Column 10,
Line 47, delete "relatives weights" and insert therefor -- relative weights --.

Column 11,
Lines 6-7, delete "is represents" and insert therefor -- represents --.
Line 18, delete "is represents" and insert therefor -- represents --.
Line 50, delete "$\eta(i,j) =$" and insert therefor -- $\mu(i,j) =$ --.

Signed and Sealed this

Eighth Day of July, 2003

JAMES E. ROGAN
*Director of the United States Patent and Trademark Office*